United States Patent [19]

Kelly

[11] 4,178,441
[45] Dec. 11, 1979

[54] ENLARGED-HETERO-RING PROSTACYLIN ANALOGS

[75] Inventor: Robert C. Kelly, Kalamazoo, Mich.

[73] Assignee: The Upjohn Company, Kalamazoo, Mich.

[21] Appl. No.: 935,296

[22] Filed: Aug. 21, 1978

Related U.S. Application Data

[60] Division of Ser. No. 819,941, Jul. 28, 1977, Pat. No. 4,124,599, which is a continuation-in-part of Ser. No. 725,547, Sep. 22, 1976, abandoned, which is a continuation-in-part of Ser. No. 716,771, Aug. 23, 1976, abandoned.

[51] Int. Cl.² .......................................... C07D 311/02
[52] U.S. Cl. .................................................. 542/426
[58] Field of Search ...................... 260/345.2; 542/426

[56] References Cited

PUBLICATIONS

Pace–Asciak et al., Biochem., 10, 3657 (1971).
Pace–Asciak et al., Jacs., 98, 2348 (1976).

*Primary Examiner*—Nicky Chan
*Attorney, Agent, or Firm*—Morris L. Nielsen

[57] ABSTRACT

Prostaglandin (PG$_1$) derivatives having (1) a 6-keto feature, together with a 9-deoxy-9-hydroxymethyl feature for example

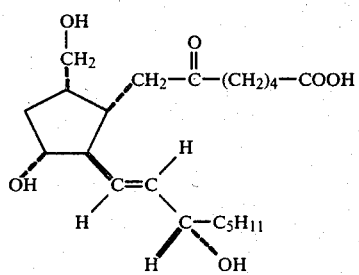

or (2) a 9-deoxy-6,9-epoxymethano feature together with a 5-halo or 6-hydroxy feature, for example

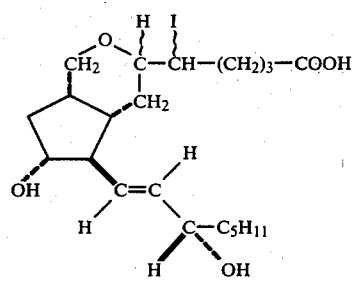

or

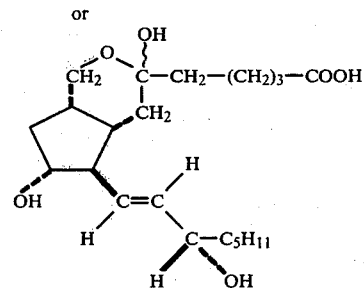

or a 5,6-didehydro feature, for example in an enol ether of the formula.

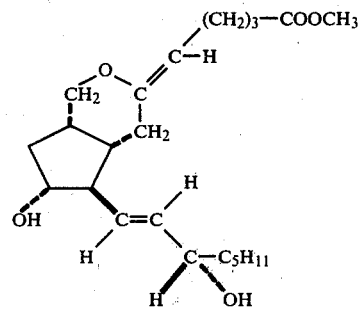

said derivatives having pharmacological activity. Processes for preparing them and the appropriate intermediates are disclosed.

17 Claims, No Drawings

ENLARGED-HETERO-RING PROSTACYLIN ANALOGS

CROSS REFERENCE TO RELATED APPLICATIONS

This is a division of application Ser. No. 819,941, filed July 28, 1977 now issued as U.S. Pat. No. 4,124,599 which is in turn a continuation-in-part of copending application Ser. No. 725,547 filed Sept. 22, 1976, now abandoned which was a continuation-in-part of then copending application Ser. No. 716,771 filed Aug. 23, 1976, since abandoned.

BACKGROUND OF THE INVENTION

This invention relates to prostaglandin derivatives and to a process for preparing them.

The prostaglandins and analogs are well-known organic compounds derived from prostanoic acid which has the following structure and atom numbering:

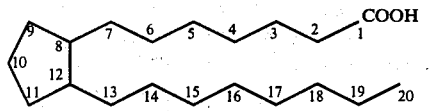

As drawn hereinafter the formulas represent a particular optically active isomer having the same absolute configuration as PGE$_1$ obtained from mammalian tissues.

In the formulas, broken line attachments to the cyclopentane ring or side chain indicate substituents in alpha configuration, i.e. below the plane of the ring or side chain. Heavy solid line attachments indicate substituents in beta configuration, i.e. above the plane.

For background on prostaglandins, see for example Bergstrom et al., Pharmacol, Rev. 20, 1 (1968). For related compounds see Pace-Asciak et al., Biochem. 10, 3657 (1971). Related compounds are described in a publication on 6-keto-prostaglandin F$_{1\alpha}$ by Pace-Asciak, J. Am. Chem. Soc. 98, 2348 (1976) and a publication on "PGX" (6,9α-oxido-9α,15α-dihydroxyprosta-(Z)5, (E)13-dienoic acid) by E. J. Corey et al., J. Am. Chem. Soc. 99, 20006 (1977).

Some of the compounds of this invention may be regarded as analogs of prostacyclin and prostacyclin-type compounds.

Prostacyclin, an organic compound related to prostaglandins, is (5Z)-9-deoxy-6,9α-epoxy-Δ$^5$-PGF$_1$ and is represented by the formula

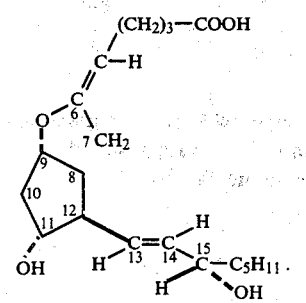

For its synthesis and structure see for example R. A. Johnson et al., J. Am. Chem. Soc. 99, 4182 (1977) and Prostaglandins 12, 915 (1976), and E. J. Corey et al., cited above. For some of its biological properties and uses see the references cited in the Johnson references. Prostacyclin is referred to as "PGI$_2$", see Anonymous, Prostaglandins 13, 373 (1977).

The essential material for this application, including the background of the invention, the disclosure of the invention, and the description of the preferred embodiments, including Preparations and Examples, is incorporated by reference from U.S. Pat. No. 4,124,599 columns 1-69, inclusive, under the provisions of M.P.E.P. 608.01(p).

SUMMARY OF THE INVENTION

It is the purpose of this invention to provide novel products having pharmacological activity. It is a further purpose to provide processes for preparing these products and their intermediates.

Accordingly, there is provided a compound of the formula:

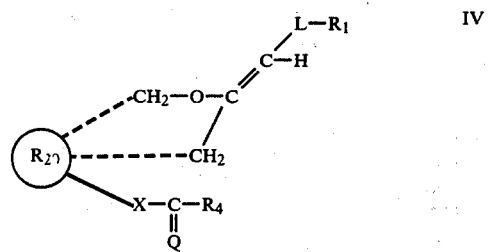

or a mixture comprising that compound and the enantiomer thereof wherein $R_{27}$ is

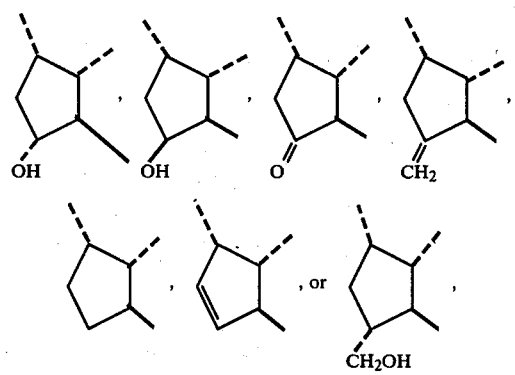

wherein
L is
(1) —(CH$_2$)$_d$—C(R$_2$)$_2$—
(2) —CH$_2$—O—CH$_2$—Y— or
(3) —CH$_2$CH=CH—
wherein d is zero to 5, R$_2$ is hydrogen, methyl, or fluoro, being the same or different with the proviso that one R$_2$ is not methyl when the other is fluoro, and Y is a valence bond, —CH$_2$— or —(CH$_2$)$_2$—,
wherein
Q is

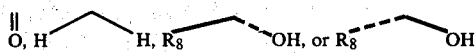

wherein
R$_8$ is hydrogen or alkyl of one to 4 carbon atoms, inclusive,
wherein $R_1$ is (1) —COOR$_3$
(2) —CH$_2$OH
(3) —CH$_2$N(R$_9$)(R$_{18}$)

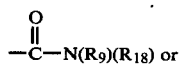 (4)

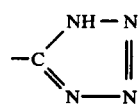 (5)

wherein R$_3$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl of one to 4 carbon atoms, inclusive,

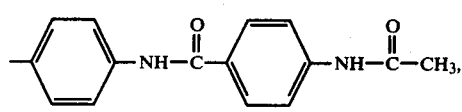 (g)

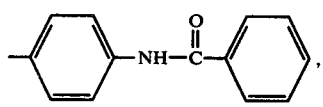 (h)

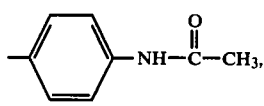 (i)

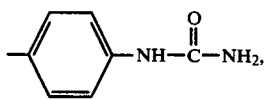 (j)

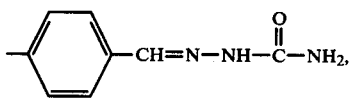 (k)

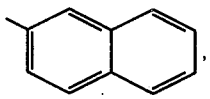 (l)

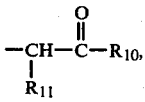 (m)

wherein R$_{10}$ is phenyl, p-bromophenyl, p-biphenylyl, p-nitrophenyl, p-benzamidophenyl, or 2-naphthyl, and wherein R$_{11}$ is hydrogen or benzoyl, or (n) a pharmacologically acceptable cation, wherein R$_9$ is hydrogen, methyl, or ethyl, and R$_{18}$ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive;
wherein R$_4$ is

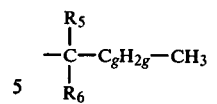 (1)

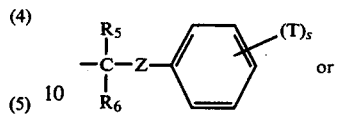 (2)

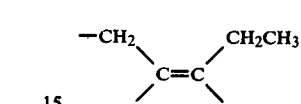 (3)

wherein C$_g$H$_{2g}$ is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro and the further proviso that neither R$_5$ nor R$_6$ is fluoro when Z is oxa (—O—); wherein Z represents an oxa atom (—O—) or C$_j$H$_{2j}$ wherein C$_j$H$_{2j}$ is a valence bond or alkylene of one to 9 carbon atoms, inclusive, with one to 6 carbon atoms, inclusive between CR$_5$R$_6$- and the phenyl ring; wherein T is alkyl of one to 4 carbon atoms, inclusive, fluoro, chloro, trifluoromethyl, or —OR$_7$— wherein R$_7$ is alkyl of one to 4 carbon atoms, inclusive, and s is zero, one, 2 or 3, with the proviso that not more than two T's are other than alkyl and when s is 2 or 3 the T's are either the same or different; and
wherein
X is
(1) trans—CH=CH—
(2) cis—CH=CH—
(3) —C≡C— or
(4) —CH$_2$CH$_2$—;
including the lower alkanoates thereof.

In formula IV as used herein, attachment to R$_{20}$ corresponds to bonds to the cyclopentane ring at the C-8, C-9, and C-12 positions following prostaglandin nomenclature, thus:

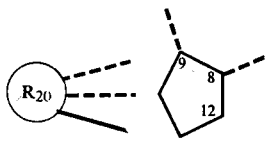

Within the scope of the prostaglandin derivatives described herein there are represented
(a) PGF$_\alpha$ compounds when 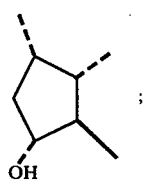 is

;

(b) 11$\beta$-PGF$_\alpha$ compounds when R$_{20}$ is (c) 11-Deoxy-11-keto-PGF$_\alpha$ compounds when R$_{20}$ is

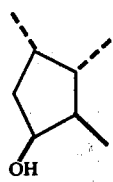

(d) 11-Deoxy-11-methylene-PGF$_\alpha$ compounds when R$_{20}$

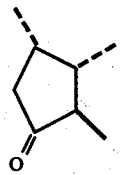

(e) 11-Deoxy-PGF$_\alpha$ compounds when R$_{20}$ is

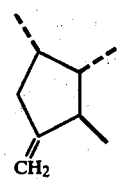

(f) 11-Deoxy-10,11-Didehydro-PGF$_\alpha$ compounds when R$_{20}$ is

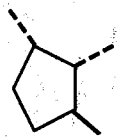

; and (g) 11-Deoxy-11-hydroxymethyl-PGF$_\alpha$ compounds when R$_{20}$ is

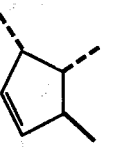

3-Oxa-16-(m-chlorophenoxy)-17,18,19,20-tetranor-cis-13-;
3-Oxa-(p-fluorophenoxy)-17,18,19,20-tetranor-cis-13-;
3-Oxa-16-phenoxy-18,19,20-trinor-cis-13-;
3-Oxa-16-methyl-16-phenoxy-18,19,20-trinor-cis-13-;

Likewise following the procedures of Examples 11, 12, and 15, but employing corresponding starting materials, there are obtained the formula -I, -II, -III, and -IV compounds, namely 9-deoxy-9$\alpha$-hydroxymethyl-6-keto-PGF$_1$-,
9-deoxy-6$\xi$,9$\alpha$-epoxymethano-6$\xi$-hydroxy-PGF$_1$-.
5$\xi$-halo-9-deoxy-6$\xi$,9$\alpha$-epoxymethano-PGF$_1$-, and
(5Z)-9-deoxy-6,9$\alpha$-epoxymethano-$\Delta^5$-PGF$_1$-type compounds, in methyl ester form wherein R$_1$ is —COOCH$_3$, having the following structural features:
2,3-Didehydro-;
2,2-Dimethyl-;
2$a$,2$b$-Dihomo-;
4-Oxa-4$a$-homo-;
11-Deoxy-10,11-didehydro-;
11$\beta$-;
11-Deoxy-11-keto-;
11-Deoxy-;
11-Deoxy-11-methylene-;
11-Deoxy-11-hydroxymethyl-;
15$\beta$-;
15-Keto-;
15-Deoxy-;
15-Methyl-15(S)-;
15-Methyl-15(R)-; and
17,18-Didehydro-.

I claim:

1. A 5Z compound of the formula

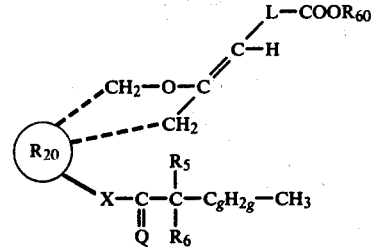

wherein R$_{20}$ is

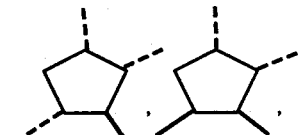

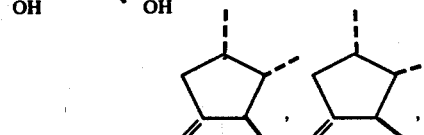

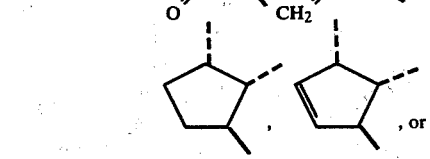

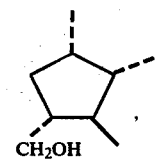

wherein
L is
(1) —(CH$_2$)$_d$—C(R$_2$)$_2$—
(2) —CH$_2$—O—CH$_2$—Y— or
(3) —CH$_2$CH=CH—
wherein d is zero to 5, R$_2$ is hydrogen, methyl, or fluoro, being the same or different with the proviso that one R₂ is not methyl when the other is fluoro, and Y is a valence bond, —CH₂— or —(CH₂)₂—, wherein Q is

wherein R₈ is hydrogen or alkyl of one to 4 carbon atoms, inclusive,
wherein
R₆₀ is (a) cycloalkyl of 3 to 10 carbon atoms, inclusive, (b) aralkyl of 7 to 12 carbon atoms, inclusive, (c) phenyl, (d) phenyl substituted with one, 2, or 3 chloro or alkyl of one to 4 carbon atoms, inclusive, (e) 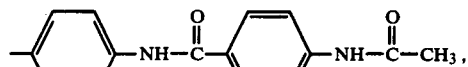

(f) 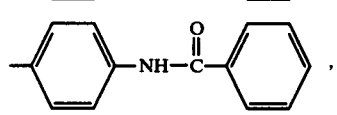

(g) 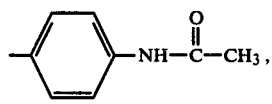

(h) 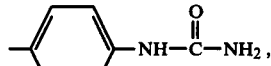

(i) 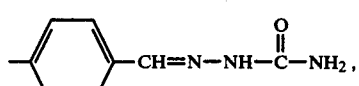

(j) 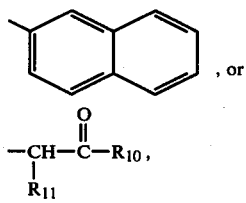, or (k)
—CH—C(=O)—R₁₀,
  |
  R₁₁ wherein R₁₀ is phenyl, p-bromophenyl, p-biphenylyl, p-nitrophenyl, p-benzamidophenyl, or 2-naphthyl, and wherein R₁₁ is hydrogen or benzoyl, wherein C_gH_{2g} is alkylene of one to 9 carbon atoms, inclusive, with one to 5 carbon atoms, inclusive, in the chain between —CR₅-R₆— and terminal methyl, wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro, and
wherein
X is
(1) trans—CH=CH—
(2) cis—CH=CH—
(3) —C≡C— or
(4) —CH₂CH₂—;
including the lower alkanoates thereof.

2. A 5E compound of the formula

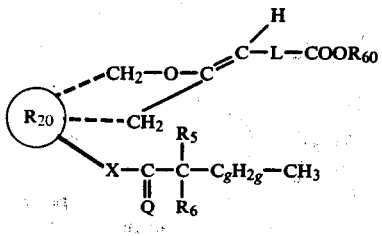

wherein R₂₀ is

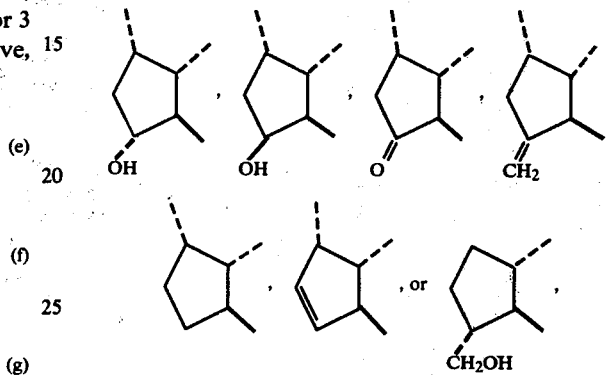

wherein
L is
(1) —(CH₂)_d—C(R₂)₂—
(2) —CH₂—O—CH₂—Y— or
(3) —CH₂CH=CH— wherein d is zero to 5, R₂ is hydrogen, methyl, or fluoro, being the same or different with the proviso that one R₂ is not methyl when the other is fluoro, and Y is a valence bond, —CH₂— or —(CH₂)₂—, wherein Q is

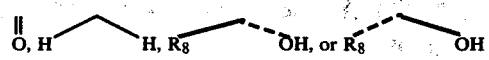

wherein
R₈ is hydrogen or alkyl of one to 4 carbon atoms, inclusive,
wherein R₆₀ is (a) cycloalkyl of 3 to 10 carbon atoms, inclusive, (b) aralkyl of 7 to 12 carbon atoms, inclusive, (c) phenyl, (d) phenyl substituted with one, 2, or 3 chloro or alkyl of one to 4 carbon atoms, inclusive, (e) 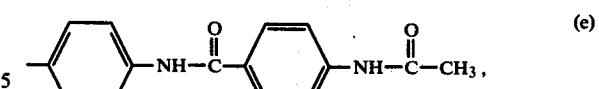

(f) 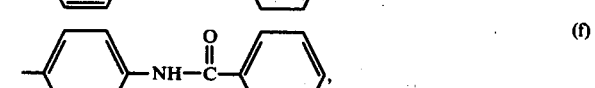

(g) 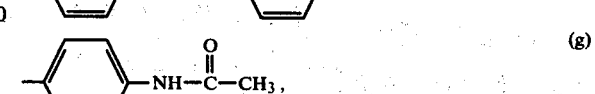

(h) 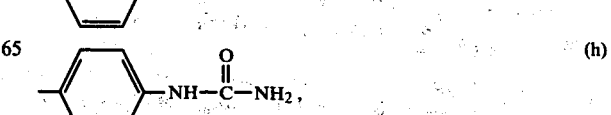

-continued

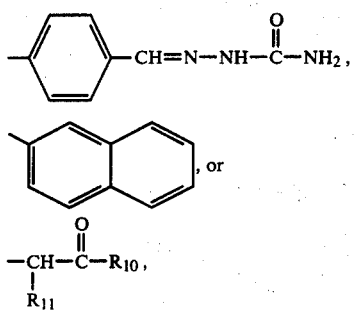

wherein R$_{10}$ is phenyl, p-bromophenyl, p-biphenylyl, p-nitrophenyl, p-benzamidophenyl, or 2-naphthyl, and wherein R$_{11}$ is hydrogen or benzoyl, wherein C$_g$H$'_{2g}$ is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro, and
wherein
X is
(1) trans—CH=CH—
(2) cis—CH=CH—
(3) —C≡C— or
(4) —CH$_2$CH$_2$—;
including the lower alkanoates thereof.

3. A compound according to claim 1 wherein R$_{20}$ is

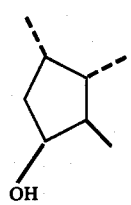

4. A compound according to claim 1 wherein R$_{20}$ is

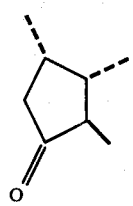

5. A compound according to claim 1 wherein R$_{20}$ is

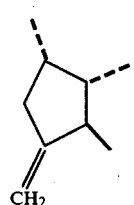

6. A compound according to claim 1 wherein R$_{20}$ is

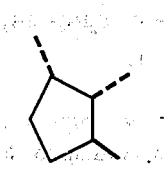

7. A compound acccording to claim 6 wherein L is —(CH$_2$)$_n$—, n being 3, 4, or 5, wherein Q is

wherein R$_8$ is limited to hydrogen, methyl, or ethyl, and wherein

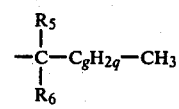

is n-pentyl, 1,1-dimethylpentyl or, 1,1-difluoropentyl.

8. A compound according to claim 1 wherein R$_{20}$ is

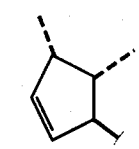

9. A compound according to claim 1 wherein R$_{20}$ is

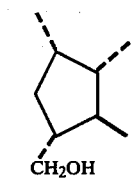

10. A compound according to claim 1 wherein R$_{20}$ is

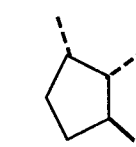

11. A compound according to claim 10 wherein L is —(CH$_2$)$_n$—, n being 3, 4, or 5, wherein Q is

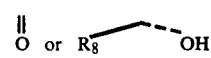

wherein R$_8$ is hydrogen, methyl, or ethyl, and wherein

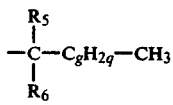

is n-pentyl, 1,1-dimethylpentyl or, 1,1-difluoropentyl.

12. A compound according to claim 11 wherein X is —C≡C—.

13. A compound according to claim 11 wherein X is —CH$_2$CH$_2$—.

14. A compound according to claim 11 wherein X is trans —CH=CH—.

15. A compound according to claim 14 wherein R$_{60}$ is

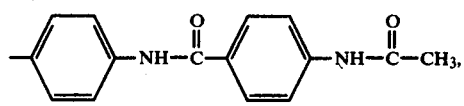

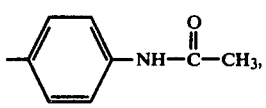

-continued

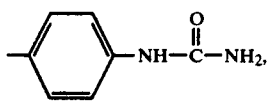

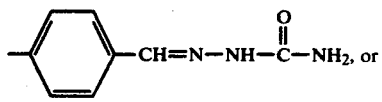

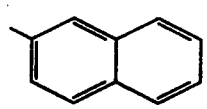

16. A compound according to claim 14 wherein R$_{60}$ is

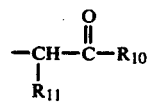

wherein R$_{10}$ and R$_{11}$ are as defined in claim 1.

17. (5Z)-9-Deoxy-6,9α-epoxy-methano-Δ$^5$-PGF$_1$, p-phenylphenacyl ester, a compound according to claim 16.

* * * * *

UNITED STATES PATENT OFFICE
CERTIFICATE OF CORRECTION

Patent No. 4,178,441　　　　　　　Dated 11 December 1979

Inventor(s) Robert C. Kelly

It is certified that error appears in the above-identified patent and that said Letters Patent are hereby corrected as shown below:

Column 4, line 41, "(3) -C=C-" should read -- (3) -C≡C- --; line 68, "$R_{20}$ is" should read -- $R_{29}$ is --.

Column 5, lines 10, 21, 31, 41, and 49, "$R_{20}$ is" should read -- $R_{29}$ is --;

Column 5, line 59, through Column 6, line 22, should be deleted.

Column 7, line 65 and Column 9, line 29, "(3) -C=C-" should read -- (3) -C≡C- --;

Column 9, lines 33, 45, and 57, "$R_{20}$ is" should read -- $R_{20}$ is --;

Column 10, lines 1, 27, 38, 48, "$R_{20}$ is" should read --$R_{29}$ is --;

Column 11, line 10, "-C=C-" should read -- -C≡C- --; line 25, the following formula should appear:

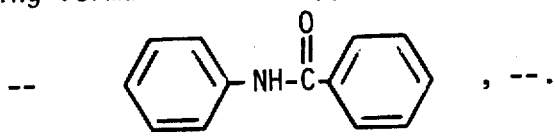

, --.

Signed and Sealed this

Twenty-third Day of December 1980

[SEAL]

Attest:

SIDNEY A. DIAMOND

Attesting Officer　　　Commissioner of Patents and Trademarks